US010780145B2

(12) United States Patent
Overstreet et al.

(10) Patent No.: US 10,780,145 B2
(45) Date of Patent: Sep. 22, 2020

(54) IN SITU FORMING HYDROGEL AND METHOD USING SAME

(71) Applicants: Arizona Board of Regents on behalf of Arizona State University, Scottsdale, AZ (US); Banner Health, Phoenix, AZ (US)

(72) Inventors: Derek Overstreet, Chandler, AZ (US); Brent Vernon, Queen Creek, AZ (US); Ryan McLemore, Phoenix, AZ (US); Alex McLaren, Scottsdale, AZ (US)

(73) Assignees: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US); BANNER HEALTH, Phoenix, AZ (US)

( * ) Notice: Subject to any disclaimer, the term of this patent is extended or adjusted under 35 U.S.C. 154(b) by 62 days.

(21) Appl. No.: 15/840,621

(22) Filed: Dec. 13, 2017

(65) Prior Publication Data

US 2018/0153956 A1    Jun. 7, 2018

Related U.S. Application Data

(63) Continuation of application No. 14/351,549, filed as application No. PCT/US2012/060124 on Oct. 12, 2012, now abandoned.

(60) Provisional application No. 61/546,402, filed on Oct. 12, 2011.

(51) Int. Cl.
 A61K 38/14 (2006.01)
 A61K 9/06 (2006.01)
 A61L 27/50 (2006.01)
 A61L 27/52 (2006.01)
 A61L 27/54 (2006.01)
 A61K 9/00 (2006.01)
 A61K 47/32 (2006.01)

(52) U.S. Cl.
 CPC ............ *A61K 38/14* (2013.01); *A61K 9/0024* (2013.01); *A61K 9/06* (2013.01); *A61K 47/32* (2013.01); *A61L 27/50* (2013.01); *A61L 27/52* (2013.01); *A61L 27/54* (2013.01); *A61L 2300/404* (2013.01); *A61L 2400/06* (2013.01); *A61L 2430/24* (2013.01)

(58) Field of Classification Search
 USPC ...................................................... 514/772
 See application file for complete search history.

(56) References Cited

U.S. PATENT DOCUMENTS

2008/0050435 A1    2/2008 Hennink et al.
2008/0096975 A1    4/2008 Guan et al.
2010/0215749 A1    8/2010 Stayton et al.

OTHER PUBLICATIONS

Huntsman technical bulletin (2007). (Year: 2007).*
Overstreet et al., (2011). "Drug delivery applications of injectable biomaterials." Injectable Biomaterials: Science and Applications 5: 95-141.
Hatefi et al., (2002). "Biodegradable injectable in situ forming drug delivery systems." J. Control. Rel. 80: 9-28.
Hoare et al., (2008). "Hydrogels in drug delivery: Progress and challenges." Polymer 49: 1993-2007.
Schild, (1992). "Poly(N-isopropylacrylamide): Experiment, Theory and Application." Prog. Polym. Sci. 17: 163-249.
Cui, Z. et al. "New hydrolysis-dependent thermosensitive polymer for an injectable degradable system", Biomacromolecules, Apr. 2007, vol. 8, pp. 1280-1286, Epub Mar. 20, 2007.
Neradovic et al., (1999). "Poly(Nisopropylacrylamide) with hydrolyzable lactid acid ester side groups: a new type of thermosensitive polymer." Macromol. Rapid Commun. 20: 577-581.
Bae, (1991). ""on-off" Thermocontrol of Solute Transport. I. Temperature Dependence of Swelling of N-Isopropylacrylamide Networks Modified with Hydrophobic Components in Water." Pharm. Res. 8: 531-537.
Bae, (1991). ""on-off" Thermocontrol of Solute Transport. II. Solute Release from Thermosensitive Hydrogels." Pharm. Res. 8: 624-628.
Okano et al., (1990). "Thermally on-off switching polymers for drug permeation and release." Journal of controlled release 11: 255-265.
Gutowska et al., (1997). "Squeezing hydrogels for controlled oral drug delivery." J. Control. Rel. 48: 141-148.
Jeong et al., (1997). "Biodegradable block copolymers as injectable drug delivery systems." Nature 388: 860-862.
Jeong et al., (1999). "New biodegradable polymers for injectable drug delivery systems." J. Control. Rel. 62: 109-114.
Jeong et al., (2000). "Drug release from biodegradable injectable thermosensitive hydrogel of PEG-PLGA-PEG triblock copolymers." J. Control. Rel. 63: 155-163.
Berbari et al., (1998). "Risk factors for prosthetic joint infection: case-control study." Clin. Infect. Dis. 27: 1247-1254.
Lentino, (2003). "Prosthetic joint infections: bane of orthopedists, challenge for infectious disease specialists." Clin. Infect. Dis. 36: 1157-1161.
Kurtz et al., (2007). "Projections of Primary and Revision Hip and Knee Arthroplasty in the United States from 2005 to 2030." J. Bone Joint Surg. Am. 89: 780-785.
Kurtz et al., (2008). "Infection burden for hip and knee arthroplasty in the United States." The Journal of Arthroplasty 23:984-991.

(Continued)

*Primary Examiner* — Marcos L Sznaidman
(74) *Attorney, Agent, or Firm* — Maschoff Brennan; Jonathan M. Benns

(57) ABSTRACT

A hydrogel (I), comprising a polymer backbone wherein an aqueous solution of the hydrogel comprises a first lower critical solution temperature, and wherein the hydrogel is configured to be converted in vivo into a modified hydrogel, and wherein an aqueous solution of the modified hydrogel comprises a second lower critical solution temperature, and wherein the second lower critical solution temperature is greater than the first lower critical solution temperature.

10 Claims, 8 Drawing Sheets

(56) References Cited

OTHER PUBLICATIONS

Henderson, E. et al. "In vivo evaluation of injectable thermosensitive polymer with time-dependent LCST", Journal of Biomedical Materials Research Part A. Sep. 15, 2009, vol. 90, Issue 4, pp. 1186-1197.
Van Vlierberghe et al., (2011). "Biopolymer-based hydrogels as scaffolds for tissue engineering applications: a review." Biomacromolecules 12: 1387-1408.
Hou et al., (2004). "Injectable scaffolds for tissue regeneration." J. Mater. Chem. 14: 1915-1923.
Nelson et al., (2011). "Intra-myocardial biomaterial injection therapy in the treatment of heart failure: Materials, outcomes and challenges." Acta Biomaterialia 7: 1-15.
Hill-West et al., (1994). "Inhibition of thrombosis and intimal thickening by in situ photopolymerization of thin hydrogel barriers." Proc. Natl. Acad. Sci. USA 91: 5967-5971.
Garrett, (2006). "American Board of Orthopaedic Surgery Practice of the Orthopaedic Surgeon: Part-II, Certification Examination Case Mix." J. Bone Joint Surg. Am. 88: 660-667.
Khanuja et al., (2011). "Cementless femoral fixation in total hip arthroplasty." J. Bone Joint Surg. Am. 93: 500-509.
Dunbar, (2009). "Cemented femoral fixation: the North Atlantic divide." Orthopedics 32: 662-665.
Font-Rodriguez et al., (1997). "Survivorship of cemented total knee arthroplasty." Clin. Orthop. Relat. Res. 345: 79-86.
Hirakawa et al., (1996). "Comparison and quantitation of wear debris of failed total hip and total knee arthroplasty." J. Biomed. Mater. Res. 31: 257-263.
Shanbhag et al., (2000). "Quantitative analysis of ultrahigh molecular weight polyethylene (UHMWPE) wear debris associated with total knee replacements." J. Biomed. Mater. Res. 53: 100-110.
Darwiche et al., (2010). "Retrospective Analysis of Infection Rate After Early Reoperation in Total Hip Arthroplasty." Clin. Orthop. Relat. Res. 468: 2392-2396.
Wasielewski et al., (1994). "Wear patterns on retrieved polyethylene tibial inserts and their relationship to technical considerations during total knee arthroplasty." Clin. Orthop. Relat. Res. 299: 31-43.
Senthi et al., (2010). "Infection in total hip replacement: meta-analysis." Int. Orthop. 35: 253-260.
Haddad et al., (2000). "Two-stage uncemented revision hip arthroplasty for infection." J. Bone Joint Surg. Br. 82: 689-694.
Kraay et al., (2005). "Cementless Two-staged Total Hip Arthroplasty for Deep Periprosthetic Infection." Clin. Orthop. Relat Res. 441: 243-249.
Bernthal et al., (2010). "A Mouse Model of Post-Arthroplasty *Staphylococcus aureus* Joint Infection to Evaluate in Vivo the Efficacy of Antimicrobial Implant Coatings." PLoS One 5: e12580.
Bozic et al., (2005). "The impact of infection after total hip arthroplasty on hospital and surgeon resource utilization." J. Bone Joint Surg. Am. 87: 1746-1751.
Gristina, (1987). "Biomaterial-centered infection: microbial adhesion versus tissue integration." Science 237: 1588-1595.
Costerton et al., (1999). "Bacterial Biofilms: A Common Cause of Persistent Infections." Science 284: 1318-1322.
Ceri et al., (1999). "The Calgary Biofilm Device: new technology for rapid determination of antibiotic susceptibilities of bacterial biofilms." J. Clin. Microbiol. 37: 1771-1776.
Cerca et al., (2005). "Comparative assessment of antibiotic susceptibility of coagulase-negative Staphylococci in biofilm versus planktonic culture as assessed by bacterial enumeration or rapid XTT colorimetry." J. Antimicrob. Microbiol. 56: 331-336.
Hanssen et al., (1998). "Instructional Course Lectures, the American Academy of Orthopaedic Surgeons—Evaluation and Treatment of Infection at the Site of a Total Hip or Knee Arthroplasty." J. Bone Joint Surg. Am. 80: 910-922.
Ong et al., (2009). Prosthetic joint infection risk after total hip arthroplasty in the Medicare population. J. Arthroplasty 24: 105-109.
Kurtz et al., (2009). "Prosthetic Joint Infection Risk after TKA in the Medicare Population." Clin. Orthop. Relat. Res. 468: 52-56.
Bourne, (2004). "Prophylactic use of antibiotic bone cement: an emerging standard—in the affirmative." J . Arthroplasty 19: 69-72.
Hanssen et al., (2004). "Practical Applications of Antibiotic-Loaded Bone Cement for Treatment of Infected Joint Replacements." Clin. Orthop. Relat. Res. 427: 79-85.
Moran et al., (1979). "Effect of Gentamicin on Shear and Interface Strengths of Bone Cement." Clin. Orthop. Relat. Res. 141: 96-101.
Penner et al., (1999). "The in vitro elution characteristics of antibiotic-loaded CMW and Palacos-R bone cements." J. Arthroplasty 14: 209-214.
Miller et al., (2011). "Surfactant-stabilized Emulsion Increases Gentamicin Elution From Bone Cement." Clin. Orthop. Relat. Res. 469: 2995-3001.
Hope et al., (1989). "Deep infection of cemented total hip arthroplasties caused by coagulase-negative staphylococci." J. Bone Joint Surg. Br. 71: 851-855.
Bohner et al., (1997). "Gentamicin-loaded hydraulic calcium phosphate bone cement as antibiotic delivery system." J. Pharm. Sci. 86: 565-572.
Barralet et al., (2002). "Effect of porosity reduction by compaction on compressive strength and microstructure of calcium phosphate cement." J. Biomed. Mater. Res. (Appl. Biomater.) 63: 1-9.
Alt et al., (2011). "Effects of gentamicin and gentamicin—RGD coatings on bone ingrowth and biocompatibility of cementless joint prostheses: An experimental study in rabbits." Acta Biomaterialia 7: 1274-1280.
Parvizi et al., (2004). "Titanium Surface with Biologic Activity against Infection." Clin. Orthop. Relat. Res. 429: 33-38.
Antoci et al., (2008). "The inhibition of *Staphylococcus epidermidis* biofilm formation by vancomycin-modified titanium alloy and implications for the treatment of periprosthetic infection." Biomaterials 29: 4684-4690.
Lucke et al., (2003). "Gentamicin coating of metallic implants reduces implant-related osteomyelitis in rats." Bone 32: 521-531.
Price et al., (1996). "Controlled release of antibiotics from coated orthopedic implants." J. Biomed. Mater. Res. 30: 281-286.
Gollwitzer et al., (2003). "Antibacterial poly(D,L-lactic acid) coating of medical implants using a biodegradable drug delivery technology." J. Antimicrob. Chemother. 51: 585-591.
De Giglio et al., (2010). "Ciprofloxacin-modified electrosynthesised hydrogel coatings to prevent titanium implant-associated infections." Acta Biomaterialia 7: 882-891.
Changez et al., (2005). "Efficacy of antibiotics-loaded interpenetrating network (IPNs) hydrogel based on poly(acrylic acid) and gelatin for treatment of experimental osteomyelitis: in vivo study." Biomaterials 26: 2095-2104.
Liu et al., (1999). "Lower critical solution temperatures of N-substituted acrylamide copolymers in aqueous solutions." Polymer 40: 6985-6990.
Feil et al., (1993). "Effect of comonomer hydrophilicity and ionization on the lower critical solution temperature of N-isopropylacrylamide copolymers." Macromolecules 26: 2496-2500.
He et al., (2008). "In situ gelling stimuli-sensitive block copolymer hydrogels for drug delivery." J. Control. Rel. 127: 189-207.
Xia et al., (2005). "Thermal response of narrow-disperse poly(N-isopropylacrylamide) prepared by atom transfer radical polymerization." Macromolecules 38: 5937-5943.
Fujishige et al., (1989). "Phase transition of aqueous solutions of poly(N-isopropylacrylamide) and poly (N-isopropylmethacrylamide)." J. Phys. Chem. 93: 3311-3313.
Comolli et al., (2009). "In vitro analysis of PNIPAAm-PEG, a novel, injectable scaffold for spinal cord repair." Acta Biomaterialia 5: 1046-1055.
Yin et al., (2006). "Poly(N-isopropylacrylamide-co-propylacrylic acid) copolymers that respond sharply to temperature and pH." Biomacromolecules 7: 1381-1385.
Park et al., (1993). "Sodium chloride-induced phase transition in nonionic poly(N-isopropylacrylamide) gel." Macromolecules 26: 5045-5048.

(56) References Cited

OTHER PUBLICATIONS

Vernon et al., (2000). "Thermoreversible copolymer gels for extracellular matrix." J. Biomed. Mater. Res. A 51: 69-79.
Qiu et al., (2006). "Polymer Architecture and Drug Delivery." Pharm. Res. 23: 1-30.
Yoshida et al., (1995). "Comb-type grafted hydrogels with rapid deswelling response to temperature changes." Nature 374: 240-242.
Reed et al., (1981). "Biodegradable polymers for use in surgery—poly(glycolic)/poly(lactic acid) homo and copolymers: 2. In vitro degradation." Polymer 22: 494-498.
Chen et al., (1995). "Temperature-induced phase transition behaviors of random vs. graft copolymers of N-isopropylacrylamide and acrylic acid." Macromol. Rapid Commun. 16: 175-182.
Weiss-Malik et al., (2004). "Independent control of lower critical solution temperature and swelling behavior with pH for poly(N-isopropylacrylamide-co-maleic acid)." J. Appl. Polym. Sci. 94: 2110-2116.
Chen et al., (1995). "Graft copolymers that exhibit temperature-induced phase transitions over a wide range of pH." Nature 373: 49-52.
Chiang et al., (2011). "Thermoresponsive Interpolymeric Complex Assemblies from Co-association of Linear PAAc Homopolymers with PNIPAAm Segments Containing PAAc-Based Graft Copolymer" Macromolecular Chemistry and Physics 212(17): 1869-1878.
Oh et al., (2012). "Temperature-sensitive hydrogel prepared by graft polymerization of N-isopropylacrylamide onto macroradical Pluronic." J. Indust. Eng. Chem. 18: 321-324.
Suzuki et al., (1999). "Shrinking pattern and phase transition velocity of poly(N-isopropylacrylamide gel)." J. Chem. Phys. 111: 360-367.
Kaneko et al., (1998). "Rapid deswelling response of poly (N-isopropylacrylamide) hydrogels by the formation of water release channels using poly(ethylene oxide) graft chains." Macromolecules 31: 6099-6105.
Stile et al., (1999). "Synthesis and characterization of injectable poly(N-isopropylacrylamide)-based hydrogels that support tissue formation in vitro." Macromolecules 32: 7370-7379.
Yoshioka et al., (1994). "A synthetic hydrogel with thermoreversible gelation. I. Preparation and Rheological Properties." J. Macromol. Sci. Pure Appl. Chem. A31: 113-120.
Brazel et al., (1996). "Pulsatile local delivery of thrombolytic and antithrombotic agents using poly (N-isopropylacrylamide-co-methacrylic acid) hydrogels." Journal of controlled release 39: 57-64.
Kim et al., (2003). "Synthesis and Characterization of Injectable Poly(N-isopropylacrylamide-co-acrylic acid) Hydrogels with Proteolytically Degradable Cross-Links." Biomacromolecules 4: 1214-1223.
Li et al., (2009). "Injectable, highly flexible, and thermosensitive hydrogels capable of delivering superoxide dismutase." Biomacromolecules 10: 3306-3316.
Gutowska et al., (1992). "Heparin release from thermosensitive hydrogels." J. Control. Rel. 22: 95-104.
Leon et al., (2009). "Phase behavior and shrinking kinetics of thereto-reversible poly(N-isopropylacrylamide-2-hydroxyethyl methacrylate)." Mater. Res. Soc. Symp. Proc. 1190.
Lee et al., (2006). "In-situ injectable physically and chemically gelling NIPAAm-based copolymer system for embolization"Biomacromolecules 7: 2059-2064.
Peeling, (1989). "Phase III studies to compare goserelin (Zoladex) with orchiectomy and with diethylstilbestrol in treatment of prostatic carcinoma." Urology 33: 45-52.
Nelson et al., (2012). "Extended and sequential delivery of protein from injectable thermoresponsive hydrogels." J. Biomed. Mater. Res. A 100: 776-785.
Morscher et al., (1998). "Severe osteolysis after third-body wear due to hydroxyapatite particles from acetabular cup coating." J. Bone Joint Surg. Br. 80: 267-272.
Landes et al., (2006). "In-patient versus in vitro degradation of P(L/DL)LA and PLGA." J. Biomed. Mater. Res. B 76: 403-411.
Heskins et al., (1968). "Solution Properties of Poly(N-isopropylacrylamide)." J. Macromol. Sci. Chem. 2: 1441-1455.
Lee et al., (2005). "Copolymers of N-isopropylacrylamide, HEMA-lactate and acrylic acid with time-dependent lower critical solution temperature as a bioresorbable carrier" Polym. Int. 54: 418-422.
Ma et al., (2010). "Thermally Responsive Injectable Hydrogel Incorporating Methacrylate-Polylactide for Hydrolytic Lability." Biomacromolecules 11: 1873-1881.
Overstreet et al., (2010). "Bioresponsive copolymers of poly (N-isopropylacrylamide) with enzyme-dependent lower critical solution temperatures." Biomacromolecules 11: 1154-1159.
Milasinovic et al., (2010). "Hydrogels of N-isopropylacrylamide copolymers with controlled release of a model protein." Int. J. Pharm. 383: 53-61.
Overstreet et al., (2013). "Temperature-responsive graft copolymer hydrogels for controlled swelling and drug delivery." Soft Materials 11: 294-304.
Kim et al., (2009). "Thermo-responsive injectable hydrogel system based on poly(N-isopropylacrylamide-co-vinylphosphonic acid). I. Biomineralization and protein delivery." J. Appl. Polym. Sci. 113: 3460-3469.
Garbern et al., (2010). "Injectable pH- and temperature-responsive poly(N-isopropylacrylamide-co-propylacrylic acid) copolymers for delivery of angiogenic growth factors." Biomacromolecules 11: 1833-1839.
Levine, (2006). "Vancomycin: A History." Clin. Infect. Dis. 42: S5-S12.
McLaren et al., (2009). "Hand-mixed and Premixed Antibiotic-loaded Bone Cement Have Similar Homogeneity." Clin Orthop. Relat. Res. 467: 1693-1698.
Jiranek et al., (2005). "Antibiotic-loaded bone cement in aseptic total joint replacement: whys, wherefores and caveats." American Academy of Orthopaedic Surgeons, Committee on Infections, 72nd Annual Meeting.
Potta et al., (2011). "Design of Polyphosphazene Hydrogels with Improved Structural Properties by Use of Star-Shaped Multithiol Crosslinkers." Macromol. Biosci. 11: 689-699.
Galperin et al., (2010). "Degradable, Thermo-Sensitive Poly(N-isopropylacrylamide)-Based Scaffolds with Controlled Porosity for Tissue Engineering Applications." Biomacromolecules 11: 2583-2592.
Denardo et al., (2003). "Effect of Molecular Size of Pegylated Peptide on the Pharmacokinetics and Tumor Targeting in Lymphoma-Bearing Mice." Clin. Cancer Res. 9: 3854S-3864S.
Peppas et al., (1993). "Preparation, structure and diffusional behavior of hydrogels in controlled release." Adv. Drug Deilv. Rev. 11: 1-35.
Lin et al., (2001). "In-Situ Thermoreversible Gelation of Block and Star Copolymers of Poly(ethylene glycol) and Poly (N-isopropylacrylamide) of Varying Architectures." Macromolecules 34: 3710-3715.
Antipas et al., (1994). "Factors affecting the deamidation of vancomycin in aqueous solutions." Int. J. Pharm. 109: 261-269.
Galanti et al., (1996). "Long-term stability of cefuroxime and cefazolin sodium in intravenous infusions." J. Clin. Pharm. Ther. 21: 185-189.
Vernon et al., (2004). "Partition-controlled progesterone release from waterborne, in situ-gelling materials." Int. J. Pharm. 274: 191-200.
Van De Belt et al., (2000). "Gentamicin release from polymethylmethacrylate bone cements and *Staphylococcus aureus* biofilm formation." Acta. Orthop. Scand. 71: 625-629.
Van De Belt et al., (2001). "*Staphylococcus aureus* biofilm formation on different gentamicin-loaded polymethylmethacrylate bone cements." Biomaterials 22: 1607-1611.
Kendall et al., (1995). "Bacterial growth on antibiotic-loaded acrylic cement: A prospective in vivo retrieval study." J. Arthroplasty 10: 817-822.
Neut et al., (2001). "Biomaterial-associated infection of gentamicin-loaded PMMA beads in orthopaedic revision surgery." J. Antimicrob. Chemother. 47: 885-891.
Hanssen, (2004). "Prophylactic use of antibiotic bone cement: an emerging standard—in opposition." J. Arthroplasty 19: 73-77.

(56) References Cited

OTHER PUBLICATIONS

Sawhney et al., (1994). "Optimization of photopolymerized bioerodible hydrogel properties for adhesion prevention." J. Biomed. Mater. Res. 28: 831-838.

Hak, (2007). "The use of osteoconductive bone graft substitutes in orthopaedic trauma." J. Am. Acad. Orthop. Surg. 15: 525-536.

Davies et al., (1989). "Influence of antibiotic impregnation on the fatigue life of simplex P and palacos R acrylic bone cements, with and without centrifugation." J. Biomed. Mater. Res. 23: 379-397.

Insall et al., (1985). "Total knee arthroplasty." Clin. Orthop. Relat. Res. 192: 13-22.

Trumpy et al., (1993). "In vivo deterioration of proplast-teflon temporomandibular joint interpositional implants: a scanning electron microscopic and energy-dispersive X-ray analysis." J. Oral Maxillofac. Surg. 51: 624-629.

Mathew et al., (1995). "Stability of Vancomycin Hydrochloride Solutions at Various pH Values as Determined by High-Performance Liquid Chromatography." Drug Dev. Ind. Pharm. 21: 257-264.

Sharkey et al., (2002). "Insall Award paper. Why are total knee arthroplasties failing today?" Clin. Orthop. Relat. Res. 404: 7-13.

Van Dyke et al., (2002). "Enhancing the value of scaling and root-planing: Arestin clinical trial results." J. Int. Acad. Periodontol. 4: 72-76.

International Preliminary Report, as issued in connection with International Patent Application No. PCT/US2012/060124, dated Apr. 24, 2014, 7 pgs.

International Search Report and Written Opinion, as issued in connection with International Patent Application No. PCT/US2012/060124, dated Mar. 15, 2013, 12 pgs.

Non-Final Office Action dated Sep. 28, 2015 in U.S. Appl. No. 14/351,549, 22 pgs.

Final Office Action dated Mar. 24, 2016 in U.S. Appl. No. 14/351,549, 24 pgs.

Non-Final Office Action dated Jan. 19, 2017 in U.S. Appl. No. 14/351,549, 31 pgs.

Final Office Action dated Jun. 16, 2017 in U.S. Appl. No. 14/351,549, 24 pgs.

Office Action dated Sep. 10, 2017 in EP Application No. 12840669.1, 4 pgs.

Supplementary European Search Report dated May 26, 2015 n EP Application No. 12840669.1.

\* cited by examiner 30 wt% poly(NIPAAm-co-DBLA-co-JAAm)

IN SITU FORMING HYDROGEL AND METHOD USING SAME

CROSS-REFERENCE TO RELATED APPLICATIONS

This application is a continuation of U.S. patent application Ser. No. 14/351,549, filed Apr. 11, 2014, which is a national stage entry of International Patent Application PCT/US2012/060124, filed Oct. 12, 2012, which claims priority to U.S. Patent Application No. 61/546,402, filed Oct. 12, 2011. These applications are incorporated herein by specific reference in their entirety.

BACKGROUND OF THE INVENTION

In situ forming hydrogels are useful for a variety of biological and biomedical applications including drug delivery, embolization, cell encapsulation and culture, and tissue regeneration.

For most applications where in situ forming hydrogels are used, resistance to shrinking is an important consideration. Usually, the ideal case is that the material transitions quickly from liquid to solid with almost no change in volume. Shrinking or swelling inherently causes changes in the hydrogel's mechanical properties, porosity, and size. Wound healing and embolization applications require retention of the hydrogel's original size at the injection site and good contact with the surrounding tissue. For controlled drug delivery, a fast sol-to-gel transition without syneresis could reduce the high initial burst release of hydrophilic drugs typical of many in situ forming materials. For successful use as synthetic extracellular matrices in vitro or in vivo, gels must retain a high volume fraction of water in order to support cell growth.

SUMMARY OF THE INVENTION

A hydrogel is presented. An aqueous solution of a polymer comprises a first lower critical solution temperature ("LCST"). When the polymer is heated above its first LCST, a hydrogel is formed. The hydrogel is configured to be converted in vivo into a modified hydrogel comprising a modified polymer, wherein an aqueous solution of the modified polymer comprises a second lower critical solution temperature ("LCST"), and wherein the second LCST is greater than the first LCST.

Applicants' hydrogel provides an in situ-forming and degradable platform for the controlled local release of drugs when dissolved in physiologically compatible aqueous solutions. Applicants' hydrogel can be used as injectable or space-filling carriers for localized delivery of antibiotics or other drugs for treatment or prevention of orthopaedic infections such as in total hip arthroplasty.

More generally, Applicants' hydrogel can be administered to nearly any location in the body where a local pathology might arise. After gelation, the resulting gel begins to release one or more medicaments. The hydrogel can also be administered to some locations in the body for long-term systemic delivery. Eventually, all the entrapped one or more medicaments are released and the gel dissolves.

The various embodiments of Applicants' hydrogel comprise a polymer with a lower critical solution temperature (LCST) in aqueous solution that is less than body temperature. At temperatures lower than the LCST, the polymer is soluble in water. When heated above the LCST, that aqueous polymer solution forms a soft and solid water-swollen hydrogel. This allows for the material to be applied or injected as a liquid and set up to form a soft solid at body temperature. In the time following injection, pendent ester groups hydrolyze to form a modified hydrogel, wherein the modified hydrogel comprises a higher LCST. As the LCST of the modified hydrogel increases above body temperature, the modified hydrogel dissolves, leaves the site of administration, and is excreted from the body via the urine.

DETAILED DESCRIPTION OF PREFERRED EMBODIMENTS

Figure 1:
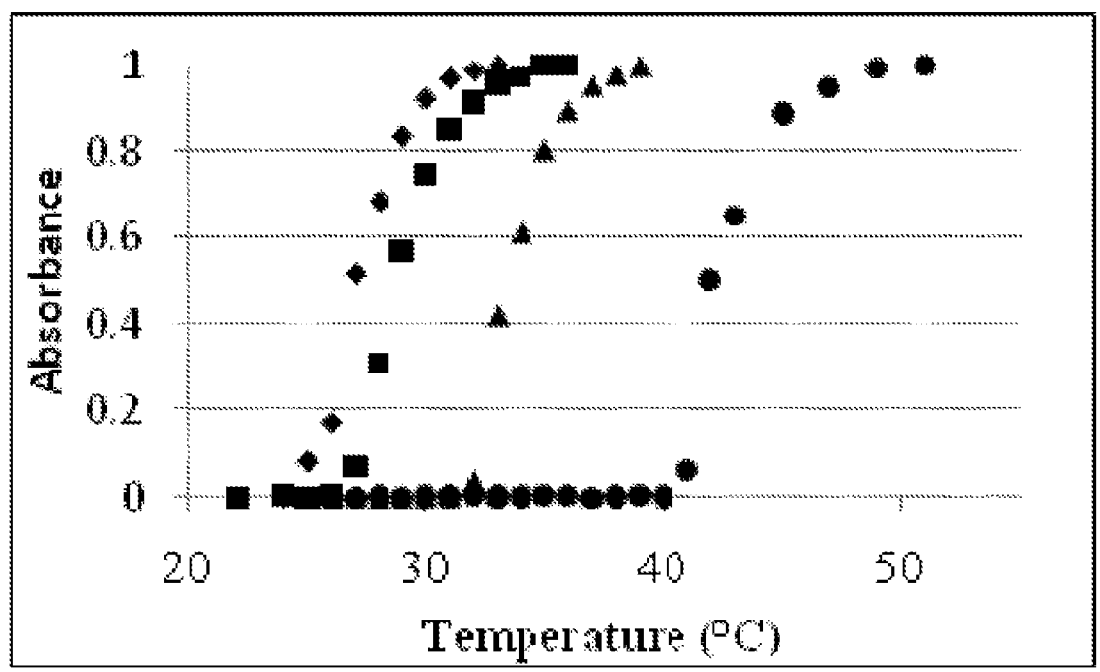
FIG. 1 graphically illustrates relative absorbance at 450 nm wavelength of 0.25 wt % solutions of Applicants' hydrogel I.

Referring to the foregoing paragraphs, this invention is described in preferred embodiments in the following description with reference to the FIGs., in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In situ forming biomaterials which transition from liquid to solid under physiological conditions are promising for a variety of medical applications, such as tissue repair, embolization, and drug delivery. Administering these materials by injection provides reduced infection risk, scar formation, and treatment cost relative to implantation. In situ forming materials can provide local, controlled delivery of therapeutics directly to the desired area with reduced risk of side effects compared with commonly performed systemic delivery. In addition to ease of administration and delivery properties, materials that form in situ are ideal for use in spaces that are irregular or difficult to access with a solid implant, since the shape of an in situ forming implant is defined by its local environment.

Aqueous solutions of temperature-responsive polymers based on N-isopropylacrylamide (NIPAAm) are particularly useful for drug delivery applications due to "outside-in" gelation which rapidly takes place in physiological conditions without low molecular weight additives or chemical reaction. NIPAAm-based polymers have a sharp lower critical solution temperature (LCST) which is relatively independent of molecular weight and concentration.

As a solution of poly(NIPAAm) is heated above its LCST (near 32° C.), polymer-polymer interactions between the hydrophobic isopropyl groups become more favorable than the polymer-water interactions with NIPAAm side group. Upon this transition, the polymer chains collapse to form a semisolid hydrogel at sufficiently high polymer concentrations for chain entanglement. Various properties such as polymer LCST, chemical reactivity, sensitivity to various stimuli (pH, enzymes), or gel swelling can be controlled by incorporating small molar fractions (<10%) of comonomers with NIPAAm in order to provide a material for a particular application. For example, hydrophobic comonomers decrease the LCST while hydrophilic comonomers increase the LCST.

Effective controlled drug delivery from poly(NIPAAm) is limited primarily by two factors: its lack of degradability and the high degree of burst release from the gels within hours after gelation. Poly(NIPAAm)-based gels crosslinked with enzyme-degradable peptides or natural biopolymers have been reported in the literature. While these gels may weaken or erode over time, the insoluble poly(NIPAAm) portions of the material will remain permanently at the injection site unless the LCST increases above body temperature, increasing the risk of chronic inflammatory response.

Fast solute release observed from poly(NIPAAm) homopolymer gels is thought to be due to changes in swelling and heterogeneity in the water distribution of the hydrophobic polymer-rich phase. A variety of drugs (including proteins) tend to release from NIPAAm-based hydrogels within one day.

Applicants have found that chemically inert hydrophilic grafts of JEFFAMINE M-1000 covalently bound to a poly (NIPAAm) backbone yield physical gels which provide slow release and controlled gel swelling with minimal LCST effects. JEFFAMINE M-1000 is a random copolymer of ethylene oxide (EO) and propylene oxide (PO) in a 19:3 EO:PO ratio with one terminal amine and one terminal methoxy group. Applicants' hydrogel represents a more clinically viable class of injectable materials for drug delivery by imparting swelling and drug release control via JEFFAMINE M-1000 in a resorbable polymer.

Applicants' have further discovered that use of substituted acrylate comonomer (R)-α-acryloyloxy-β,β-dimethyl-γ-butyrolactone (DBLA) increases the LCST of Applicants' hydrogel I as a result of a ring-opening mechanism which converts hydrogel I into a modified hydrogel and a provides an increased LCST without the loss of low molecular weight byproducts. In this design, only a small molar fraction (<10%) of side groups on the polymer become ionized at physiological pH to cause dissolution of the polymer, which may provide improved biocompatibility over using degradable polyesters such as poly(lactic acid).

One application where Applicants' in situ forming materials can meet clinical need is in the prevention and management of orthopaedic infections. For example, total hip arthroplasty (THA) is a very common procedure, with more than 200,000 performed in the US each year. By 2030, this number is estimated to increase to 572,000. The incidence of prosthetic joint infection in total hip and total knee arthroplasties is approximately 1.5-2.5% for primary interventions and higher for revision procedures performed secondary to infection. While the incidence of infection is relatively low, the high number of operations overall combined with the high cost of treating an infected arthroplasty (over $50,000 in Year 1995 dollars) make this an area of great need. As the majority of primary THAs are now cementless (where the hip prosthesis is fit directly into the intramedullary space), there is no opportunity for delivery of antibiotics to the surface of the prosthesis via antibiotic-loaded acrylic bone cement. In addition to its role as a fixative and structural element, bone cement is commonly used in orthopaedic surgery as a carrier for antibiotics and antifungal agents, despite the fact that only a small fraction of the entrapped drug is released, and the elution rate is very low after the first day.

It would be of great benefit to be able to locally deliver drugs using a resorbable material around orthopaedic implants during or even after these common procedures. Toward this goal, Applicants have developed a polymer formulation based on NIPAAm, JAAm, and DBLA which has properties suitable for an in situ forming hydrogel for orthopaedic applications—specifically, the following: 1) efficient and sustained antibiotic release compared to bone cement, 2) soft yet cohesive physical structure so it can act as a "filler" capable of fitting into a variety of small or irregular locations where cement may not be able to access, and 3) degradability. The method of use for this class of materials is novel in itself because there are currently no such soft and degradable vehicles for drug delivery available on the market. These materials provide an advantage for some medical conditions limited to small areas of the body because they can be easily applied/injected and they then will thicken/gel and entirely fill the irregular space into which they are placed.

R1 and R2 are independently selected from the group consisting of H, alkyl, phenyl, benzyl, 2-cyanoprop-2-yl, 4-cyanopentanoic acid-4-ylethyl-2-propionate, sulfate, 2-[2-methoxypropan-2-yl)oxy]propan-2-yl, and a dithioester derived from a RAFT chain transfer agent such as 4-cyano-4-(ethylsulfanylthiocarbonyl) sulfanylpentanoic acid.

In certain embodiments, pendent group R8 comprises a linkage with the polymer backbone selected from the group consisting of an ester, amide, thioamide, thiourea, anhydride, thioester, thiourea, and alkyl. In certain embodiments, pendent group R8 comprises at least one ester or anhydride.

In certain embodiments, linkage R8 is selected from the group consisting of ester, amide, thioamide, thiourea, anhydride, thioester, thiourea, and alkyl. In certain embodiments, either linkage R8 or pendent group R6 comprises at least one ester or anhydride.

In certain embodiments, R6 is selected from the group consisting of alkyl, phenyl, polyesters, and lactones. In certain embodiments, R6 comprises a substituted butyrolactone.

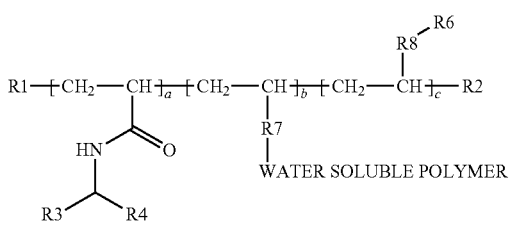

I

In certain embodiments, R7 comprises an amide linkage. In certain embodiments, R7 comprises a thioamide linkage. In certain embodiments, R7 comprises a urea linkage. In certain embodiments, R7 comprises a thiourea linkage. In certain embodiments, R7 comprises an ester linkage. In certain embodiments, R7 comprises an anhydride linkage.

In certain embodiments, the water soluble polymer comprises a polyether. In certain embodiments, the water soluble polymer comprises polyether II formed by ring opening polymerization of ethylene oxide, wherein R9 is selected from the group consisting of H, methyl, methoxy, and hydroxyl. In certain embodiments, n is between about 5 and about 2500.

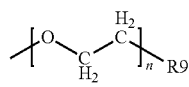

II

In certain embodiments, the water soluble polymer comprises polyether III formed by ring opening polymerization of propylene oxide. In certain embodiments, n is between about 15 and about 250.

III

In certain embodiments, the water soluble polymer comprises polyether IV formed by co-polymerization of ethylene oxide and propylene oxide. In certain embodiments r is between about 5 and about 2500, and p is between about 1 and about 1000.

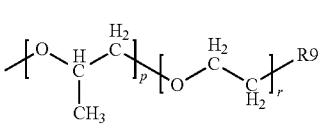

IV

In certain embodiments, the water soluble polymer comprises polyether V formed by ring opening polymerization of tetrahydrofuran. In certain embodiments, n is between about 10 and about 50.

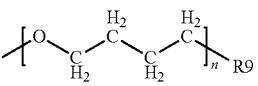

V

In certain embodiments, the water soluble polymer comprises a water-soluble polymer of one or more of the following: vinyl alcohol, acrylic acid, methacrylic acid, 2-hydroxyethyl methacrylate, N-2 hydroxypropylmethacrylamide, vinylpyrrolidone, or a monosaccharide.

In certain embodiments, graft terpolymer I comprises a plurality of repeat units VI formed using monomer VII, a plurality of repeat units IX formed using monomer X, and a plurality of repeat units XI using monomer XII.

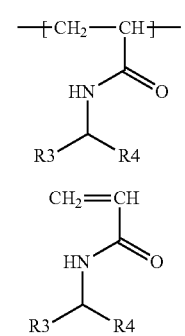

VI

VII

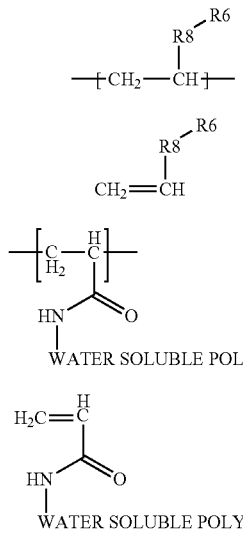

IX

X

XI

XII

In certain embodiments, graft terpolymer I comprises a plurality of repeat units VI formed using monomer VII, a plurality of repeat units IX formed using monomer X, and a plurality of repeat units XIII using monomer XIV.

XIII

-continued

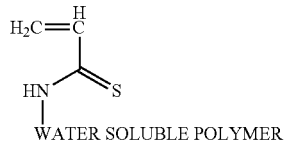

XIV

In certain embodiments, graft terpolymer I comprises a plurality of repeat units VI formed using monomer VII, a plurality of repeat units IX formed using monomer X, and a plurality of repeat units XV using monomer XVI.

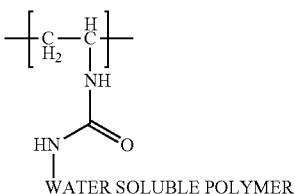

XV

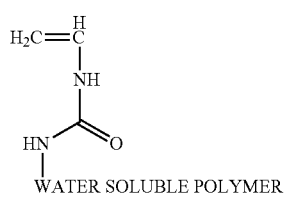

XVI

In certain embodiments, graft terpolymer I comprises a plurality of repeat units VI formed using monomer VII, a plurality of repeat units IX formed using monomer X, and a plurality of repeat units XVII using monomer XVIII.

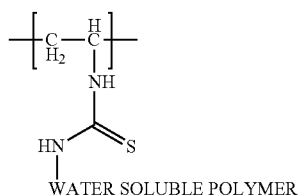

XVII

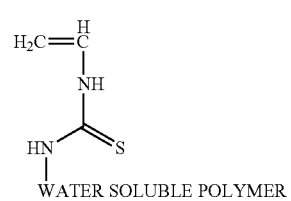

XVIII

In certain embodiments, graft terpolymer I comprises a plurality of repeat units VI formed using monomer VII, a plurality of repeat units IX formed using monomer X, and a plurality of repeat units XIX using monomer XX.

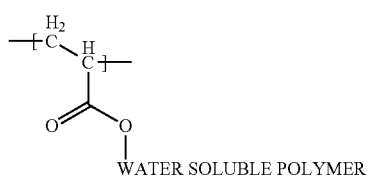

XIX

XX

In certain embodiments, graft terpolymer I comprises a plurality of repeat units VI formed using monomer VII, a plurality of repeat units IX formed using monomer X, and a plurality of repeat units XXI using monomer XXII.

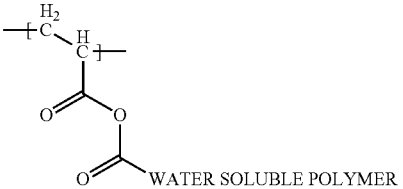

XXI

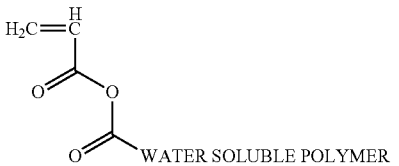

XXII

In certain embodiments, a is between about 10 and about 1000, b is between about 1 and about 250, and c is between about 1 and about 500.

Terpolymer I can be synthesized via a number of different procedures. For example, Applicants' graft terpolymer I can be prepared by free radical polymerization.

Graft terpolymer I can also be prepared by reversible addition-fragmentation chain transfer ("RAFT") polymerization. Those skilled in the art will appreciate that a RAFT polymerization can be performed by adding a quantity of a RAFT agent (thiocarbonylthio compounds) to a conventional free radical polymerization. Usually the same monomers, initiators, solvents and temperatures can be used. Because of the low concentration of the RAFT agent in the system, the concentration of the initiator is usually lower than in conventional radical polymerization. Radical initiators such as azobisisobutyronitrile (AIBN) and 4,4'-Azobis(4-cyanovaleric acid) (ACVA) which is also called 4,4'-Azobis(4-cyanopentanoic acid) are widely used as the initiator in RAFT. RAFT polymerization is known for its compatibility with a wide range of monomers, including for example acrylates and acrylamides.

Graft terpolymer I, as either a random copolymer or a block copolymer, can also be prepared by atom transfer radical polymerization ("ATRP"). Controlled polymerization of N-isopropylacrylamide (NIPAAM) by atom (ATRP) can be effected using ethyl 2-chloropropionate (ECP) as initiator and CuCl/tris(2-dimethylaminoethyl)amine (Me₆TREN) as a catalytic system. The living character of the polymerization allows preparation of block copolymers.

The following examples are presented to further illustrate to persons skilled in the art how to make and use the invention. These examples are not intended as a limitation, however, upon the scope of the invention.

Examples

An embodiment of Applicant's hydrogel I comprises a random terpolymer formed using three monomers, namely N-isopropylacrylamide (NIPAAm), JEFFAMINE M-1000 acrylamide (JAAm), and acryloyloxy-$\beta,\beta$-dimethyl-$\gamma$-butyrolactone (DBLA). JAAm is synthesized prior to synthesis of the entire polymer. All materials were reagent grade and can be obtained from Sigma-Aldrich unless otherwise noted.

NIPAAm monomer was recrystallized from hexane. Azobisisobutyronitrile (AIBN) was recrystallized from methanol. HPLC grade tetrahydrofuran (THF) was used for low molecular weight polymerizations and as the mobile phase for molecular weight and polydispersity determination. JEFFAMINE M-1000 polyetheramine was donated by Huntsman Corporation (The Woodlands, Tex. USA).

JEFFAMINE M-1000 acrylamide (JAAm) was synthesized from JEFFAMINE M-1000 polyetheramine by acryloylation with acryloyl chloride. JEFFAMINE M-1000 (20 g, 20 mmol) was dissolved at 10 w/v % in dichloromethane (DCM) along with triethylamine (3.3 mL, 24 mmol) and maintained at 0° C. under nitrogen atmosphere. Acryloyl chloride (1.95 mL, 24 mmol) was then added dropwise into the solution under stirring and the reaction was allowed to proceed for 1 hour at 0° C. and then at room temperature for at least 5 hours under nitrogen atmosphere. Following the reaction, DCM was evaporated and the remaining residue was dissolved in 0.1 N sodium bicarbonate (200 mL). The product was extracted into DCM and the organic phase purified by column chromatography. After evaporation of DCM under mild heating at reduced pressure. JAAm was obtained as a viscous clear to light yellow liquid. JAAm was solidified by cooling on ice, vacuum dried overnight, then collected and stored at −20° C.

Hydrogel I prepared using NIPAAm, DBL, and JAAm were synthesized by radical polymerization with 80% dioxane/20% THF as the solvent, but other solvents may be used, including methanol, ethanol, water, benzene, acetone, isopropanol, pure dioxane, pure tetrahydrofuran, or others. All three monomers (NIPAAm, DBLA, and JAAm) were dissolved in the solvent. Monomer solution (10 w/v %) was bubbled with nitrogen for at least 10 minutes prior to addition of initiator to reduce dissolved oxygen. After this time, AIBN (initiator) was added (~0.007 mol AIBN/mol of total monomer) and the reaction allowed to proceed for 24 hr at 65° C. under a slight positive pressure of nitrogen.

Applicants' hydrogel was collected by precipitation into 10 to 15-fold excess of a solvent in which the polymer is not soluble, such as chilled diethyl ether or hexane. Following precipitation, the product was collected by filtration and dried overnight under vacuum. The product was then dissolved in deionized water and can optionally be dialyzed against 3500 MWCO at 4° C. for 20 hours with the excess water replaced 3 times in order to purify the material, removing any low molecular weight impurities. Materials were then lyophilized and can be stored at −20° C. under nitrogen atmosphere until use.

To prepare a solution for antibiotic delivery, the materials can be sterilized (such as by ethylene oxide gas sterilization) and then dissolved in 150 mM phosphate buffered saline (pH 7.4). After dissolution of the polymer, drug powder (finely ground) is added directly to the polymer solution and vortex mixed to distribute the drug evenly throughout the solution. The solutions can be stored in a freezer until use and thawed at the time of use. The solution then can be injected, brushed, poured, sprayed, or otherwise administered as a liquid at the desired site. The solution can also be allowed to warm to above its initial LCST and then implanted as a soft hydrogel at the desired site. Examples of desired sites for delivery of this material might include the surface of a joint prosthesis, the intramedullary canal before implantation of a prosthesis, an infected area, or any location deemed to have a risk of future infection. An example formulation might be a 30 wt % polymer solution with approximately 50 mg vancomycin hydrochloride loaded per mL of polymer solution.

Hydrogels are defined as three-dimensional (3D), water-swollen polymer networks formed as a result of physical or chemical cross-linking. Because of their high water content and mechanical resemblance to natural tissues, hydrogels show promising biocompatibility and potential for medical applications. Injectable hydrogel formulations are especially attractive due to their minimally invasive delivery procedure, providing reduced healing time, reduced scarring, decreased risk of infection, and ease of delivery compared with surgically implanted materials.

Injection of viscoelastic fluids, most commonly lightly pre-crosslinked hyaluronic acid, into joints has been performed for over 20 years in the treatment of osteoarthritis. These viscosupplementation treatments are said to derive their effectiveness in part from the high viscosity of the injected polymer solution.

Polymeric hydrogels which undergo crosslinking during or after administration to a joint space may represent an improvement because such hydrogels undergoes an increase in viscosity within the joint space following administration. Thus the hydrogel precursor may be administered as a relatively less viscous liquid, then forming a much more viscous or viscoelastic gel within a timeframe of less than one hour. Additionally, this higher viscosity imparted by crosslinking in siru could lead to prolonged residence time in the joint and therefore a longer treatment duration achieved with a single administration.

Some in situ crosslinking hydrogels (including the Applicants' terpolymer hydrogels) are viscoelastic, providing properties that can allow for the gel to remain intact within the joint by yielding during joint motion, conforming to the shape of the joint space in a way that is analogous to a highly viscous liquid. Because of their rheological properties, viscoelastic hydrogels are especially well-suited to conform to the surface of a prosthetic joint (or other surfaces present in a joint) to provide effective and sustained local concentrations of drug within the joint.

In certain embodiments, Applicants utilize a crosslinked hydrogel injected into a joint space. By "crosslinked hydrogel" Applicants mean a physically or chemically crosslinked polymer-containing material containing over 50 weight percent of an aqueous solvent. In certain embodiments, the gel is crosslinked prior to injection. In certain embodiments, the gel is crosslinked after injection in the joint space.

Applicants' method administers a hydrogel in vivo to a joint space of an animal. In certain embodiments, the hydrogel forms by physical crosslinking (for example, by heating above an LCST). In certain embodiments, the crosslinked hydrogel forms by supramolecular self-assembly. In certain embodiments, the crosslinked hydrogel forms by covalent crosslinking.

In certain embodiments, the crosslinked hydrogel is administered by transcutaneous injection. In certain embodiments, the crosslinked hydrogel is administered to the joint space during a surgical procedure.

In certain embodiments, the crosslinked hydrogel contains no medicament. In certain embodiments, the crosslinked hydrogel comprises a medicament. In certain embodiments, the medicament comprises an antimicrobial.

In certain embodiments, the crosslinked hydrogel is administered to the hip joint in conjunction with total hip arthroplasty. In certain embodiments, the crosslinked hydrogel is administered to the knee joint in conjunction with total knee arthroplasty. In certain embodiments, the joint space is the hip joint. In certain embodiments, the joint space is the knee joint.

effectively target the implant surface and can cause toxicity and side effects at a dose that would be therapeutic at the implant surface.

There are four major problems with using bone cement for antibiotic delivery. First, the drug release is inefficient, meaning that a low fraction (~10% for prophylactic "low" doses and ~40% for "high" doses) of the drug mixed into the cement is ever released. The remaining drug gets trapped deep inside the cement. This is wasteful because most of the drug purchased is never released from the cement. As a result, most of the entrapped drug is not released in a concentration sufficient to provide therapeutic benefit.

Second, drug release is not sustained. Drug must be maintained at the site of infection at as a high concentration for as long of a time as possible in order to destroy a

TABLE 1

Selected properties of degradable temperature-responsive polymers with and without JAAm.

| Polymer | Feed ratio (mol %) | | Composition* (mol %) | | Molecular weight (g/mol) | | Initial LCST (° C.) | Degradation time (37° C., pH 7.4) |
|---|---|---|---|---|---|---|---|---|
| | DBLA | JAAm | DBLA | JAAm | $M_n$ | $M_w$ | | |
| poly(NIPAAm-co-DBLA) | 7.2 | — | 5.6 | 0.0 | 13,100 | 32,100 | 18 | ~20 weeks** |
| poly(NIPAAm-co-DBLA-co-JAAm) | 7.1 | 4.1 | 4.7 | 2.9 | 13,100 | 28,200 | 27 | 8-10 days |

*Measured by $^1$H NMR,
**estimated using accelerated degradation study (ISO 10993)

Approximately 800,000 arthroplastics overall were performed in the United States in 2003 alone. Approximately 1.5-2.5% of these fail due to infection, which causes loosening of the implant. Now that the vast majority of hip prostheses rely on cementless fixation of the femoral component, there is no clinically available material which allows for delivery of drugs at the implant surface where most infections arise. While cemented fixation is common in total knee arthroplasty, most of the implant surface is not in contact with the cement, and effective local concentrations are not achieved. Even in situations where bone cement can be used, the rate of drug release is very slow after the first 1-2 days, which may limit its effectiveness in preventing or managing infection.

Once a prosthetic joint is implanted and reaches body temperature, Applicants' injected hydrogel I, in solution, becomes a soft semi-solid filler which steadily delivers antibiotics directly at the surface of the implant which may do so without disrupting the fit between the bone and the prosthesis or generating wear debris from joint motion. By delivering the antibiotics directly at the implant surface, the drug concentration near the implant can be maintained at a high level in order to prevent infection, while the systemic exposure to the drug (and the corresponding side effects) can remain low.

The only existing product widely used clinically for either prevention or management of orthopaedic infections is poly (methyl methacrylate) (PMMA) bone cement, which is marketed and sold in a variety of formulations. The drug(s) (antibiotics or antifungals) are finely ground and mixed into the cement before implantation. Local delivery of drugs (drugs administered near the implant site) is required in order to provide high drug concentration at the desired site with low concentration elsewhere in the body. Systemic administration (such as by intravenous infusion) does not bacterial biofilm, which can require 1000 times as much drug concentration to inhibit growth as an individual planktonic bacterium. Most of the drug release from cement occurs within the first 1-2 days, with very low release thereafter.

Third, bone cement is not degradable. While bone cement is known to be biocompatible, it cannot be used with cementless hip stems and is not re-dosable without an invasive procedure.

Finally, bone cement is not indicated for use with many cementless hip prosthesis designs.

An aqueous solution of Applicants' injectable hydrogel composition I overcomes the deficiencies of prior art bone cement. Applicants' hydrogel I provides efficient drug release. Because the material eventually dissolves, all of the drug is eventually delivered and utilized. Local delivery provides the highest drug concentration directly where it is needed—at the implant surface.

Applicants' hydrogel provides sustained drug release. Throughout the 7-10 day period during which the material dissolves, drug is released at a relatively steady rate, which may provide improved performance at preventing or managing prosthetic joint infections.

Applicants' hydrogel provides local delivery to the implant surface of cementless stems without disrupting the quality of fit between the hip prosthesis and the femur.

Applicants' hydrogel provides degradability. Previous work by Applicants' and colleagues has shown no difference in immune response from that of native tissue following gel dissolution. The degradability of the material also allows for it to be re-dosable by transcutaneous injection in some cases.

FIG. 1 graphically illustrates relative absorbance of 0.25 wt % solutions of Applicants' hydrogel I comprising poly (NIPAAm-co-DBLA-co-JAAm) with 5.9 mol % DBLA, 2.3 mol % JAAm incubated at 37° C. in Phosphate Buffer Solution after 1 day (◆), 3 days (■), 7 days (▲), and 15 days (●). DBLA is dimethyl-butyrolactone acrylate and JAAm is JEFFAMINE M-1000 acrylamide.

Figure 2:
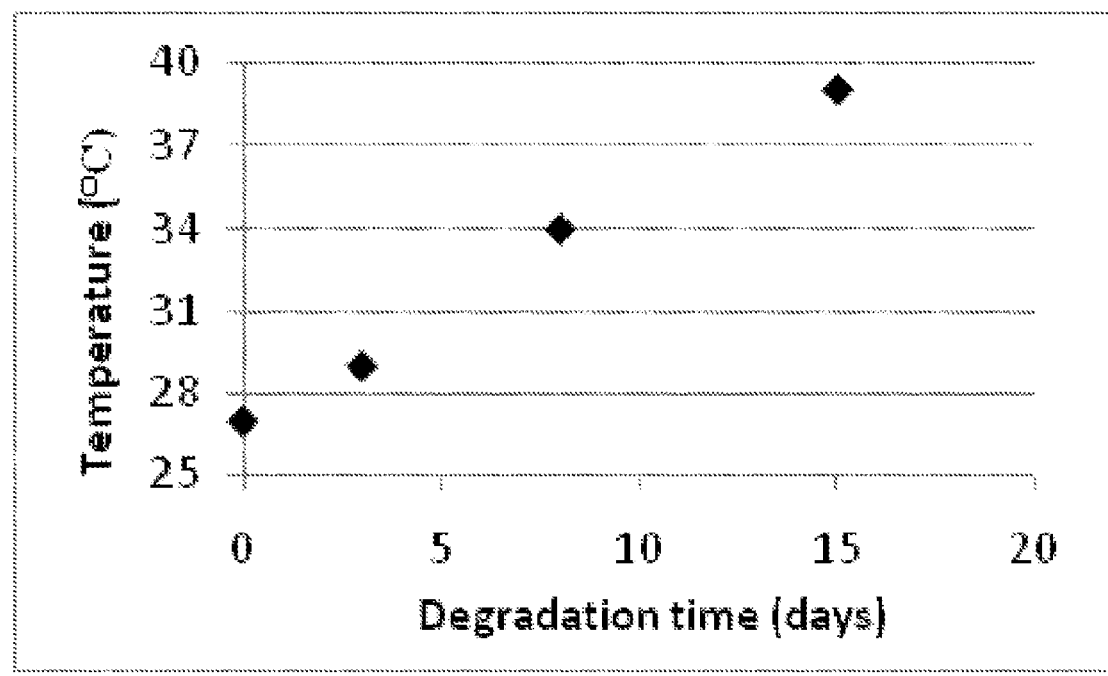
FIG. 2 shows a LCST of 5 wt % solutions of poly(NIPAAm-co-DBLA-co-JAAm) with 5.9 mol % DBLA, 2.3 mol % JAAm determined by cloud point as a function of time, wherein NIPAAm is N-isopropylacrylamide, DBLA is (R)-$\alpha$-Acryloyloxy-$\beta,\beta$-dimethyl-$\gamma$-butyrolactone, and JAAm is Jeffamine M-1000 acrylamide.

FIG. 2 shows the LCST of 5 wt % solutions of poly (NIPAAm-co-DBLA-co-JAAm) with 5.9 mol % DBLA, 2.3 mol % JAAm determined by cloud point as a function of time. As a comparison, the LCST for the same polymer without JAAm remains at 18° C. for the first 2 weeks. As those skilled in the art will appreciate, human body temperature is about 37° C. When the LCST of Applicants' injected hydrogel I increases to above 37° C., material injected into the body will dissolve.

Figure 3:
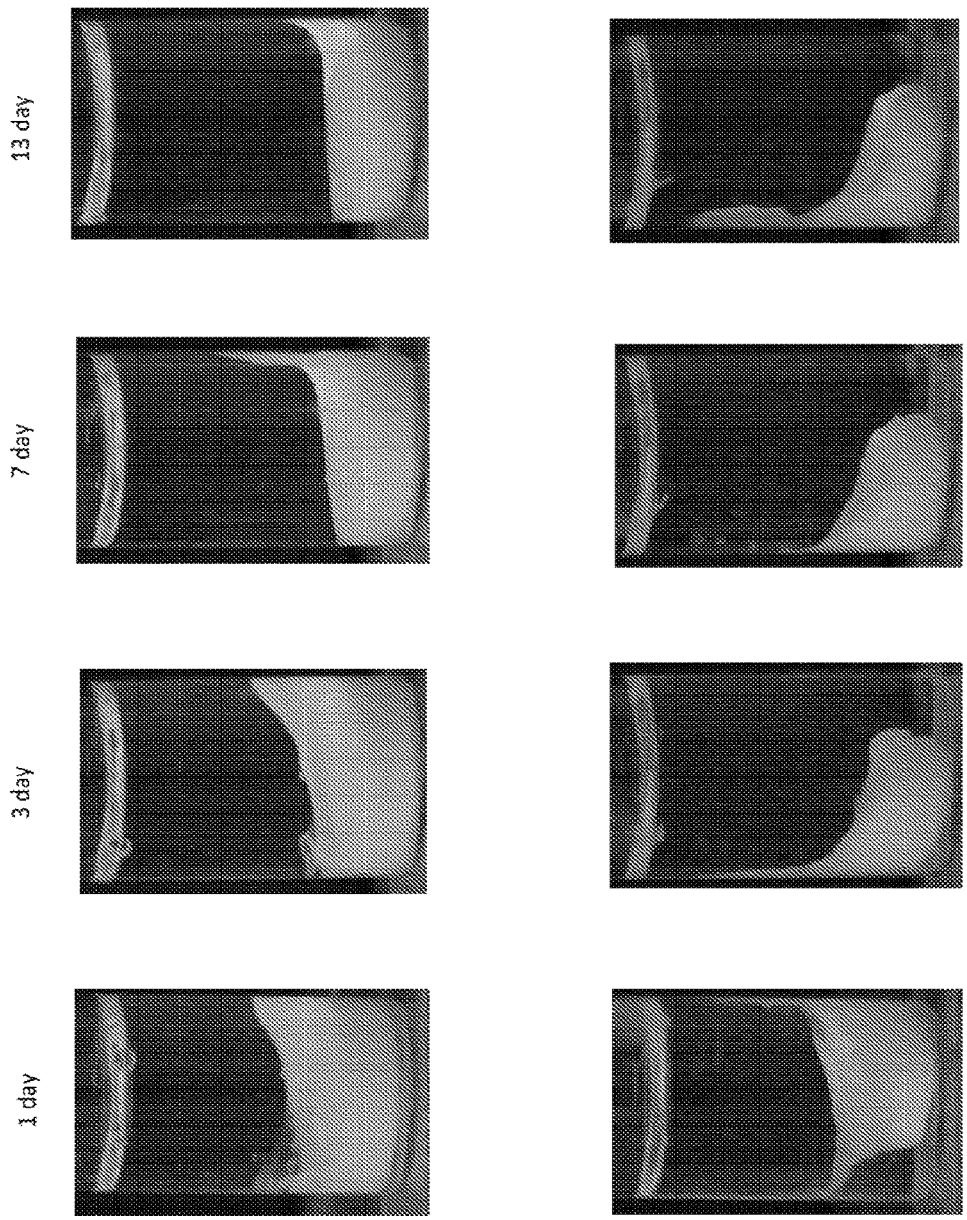
FIG. 3 shows swelling of a control polymer 30 wt % poly(NIPAAm-co-DBLA) at various times after gelation in excess PBS (pH 7.4) at 37° C.

FIG. 3 shows swelling of a control polymer 30 wt % poly(NIPAAm-co-DBLA) at various times after gelation in excess PBS (pH 7.4) at 37° C. The control copolymer comprises no absence of JAAm. Gels began shrinking rapidly beginning on the first day. These gels dissolve in approximately 20 weeks.

Figure 4:
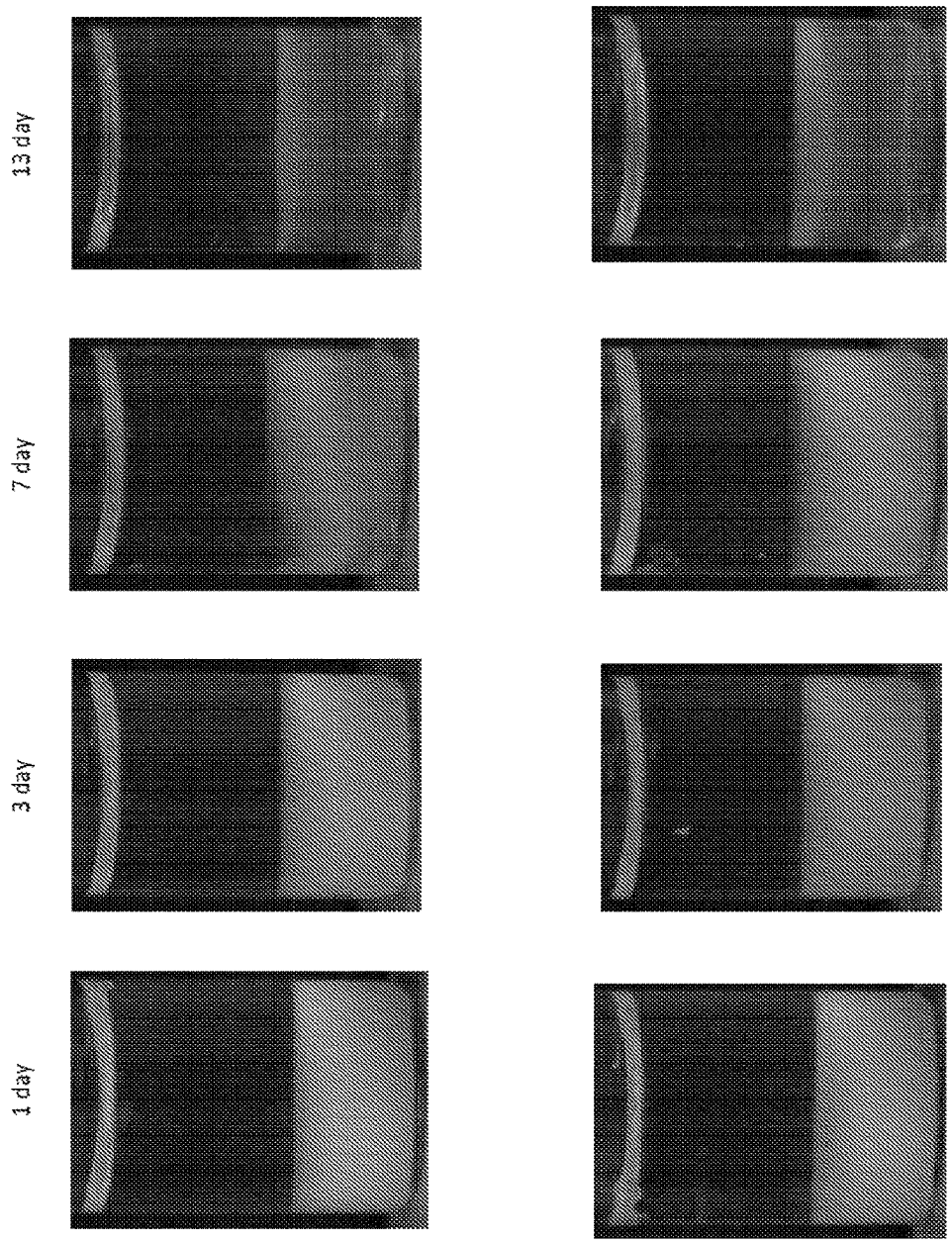
FIG. 4 shows swelling and degradation behavior of Applicants' terpolymer I based gel comprising poly(NIPAAm-co-DBLA-co-JAAm) in excess PBS (pH 7.4)

FIG. 4 shows swelling and degradation behavior of Applicants' terpolymer I based gel comprising poly(NIPAAm-co-DBLA-co-JAAm) in excess PBS (pH 7.4). Gels retained their initial volume throughout the study and underwent bulk degradation. Gels flow when inverted after 7-10 days and dissolve completely within 2-3 weeks.

Figure 5:
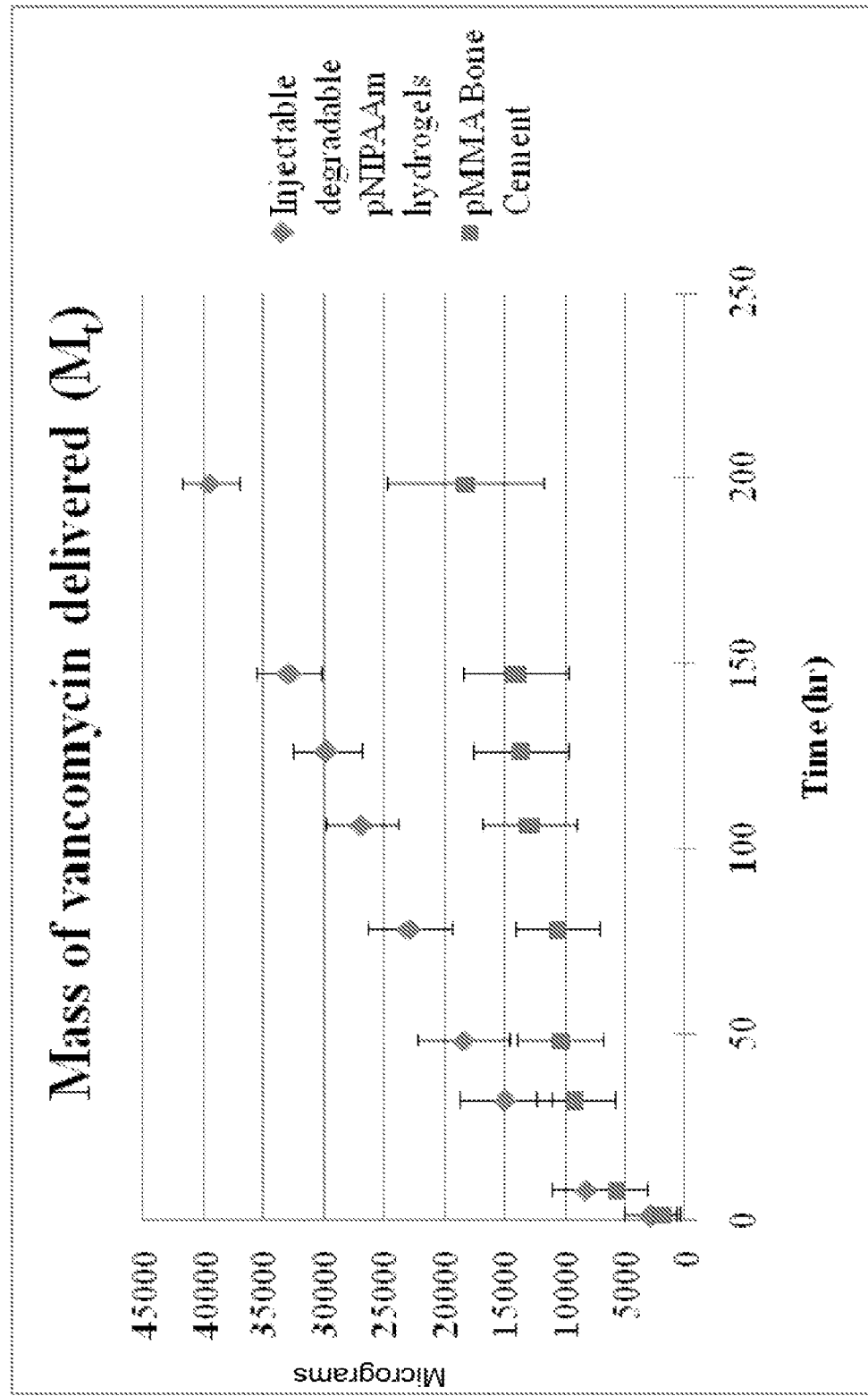
FIG. 5 graphically illustrates the mass of vancomycin released from 1 mL gels loaded with 50,000 micrograms vancomycin HCl and 1 mL bone cement samples loaded with 142,000 micrograms vancomycin HCl.

FIG. 5 graphically illustrates the mass of vancomycin released from 1 mL gels loaded with 50,000 micrograms vancomycin HCl and 1 mL bone cement samples loaded with 142,000 micrograms vancomycin HCl. Release is prolonged and increased from Applicants' injectable and degradable terpolymer I based gels comprising poly(NI-PAAm-co-DBLA-co-JAAm) as compared to clinically used bone cement.

Figure 6:
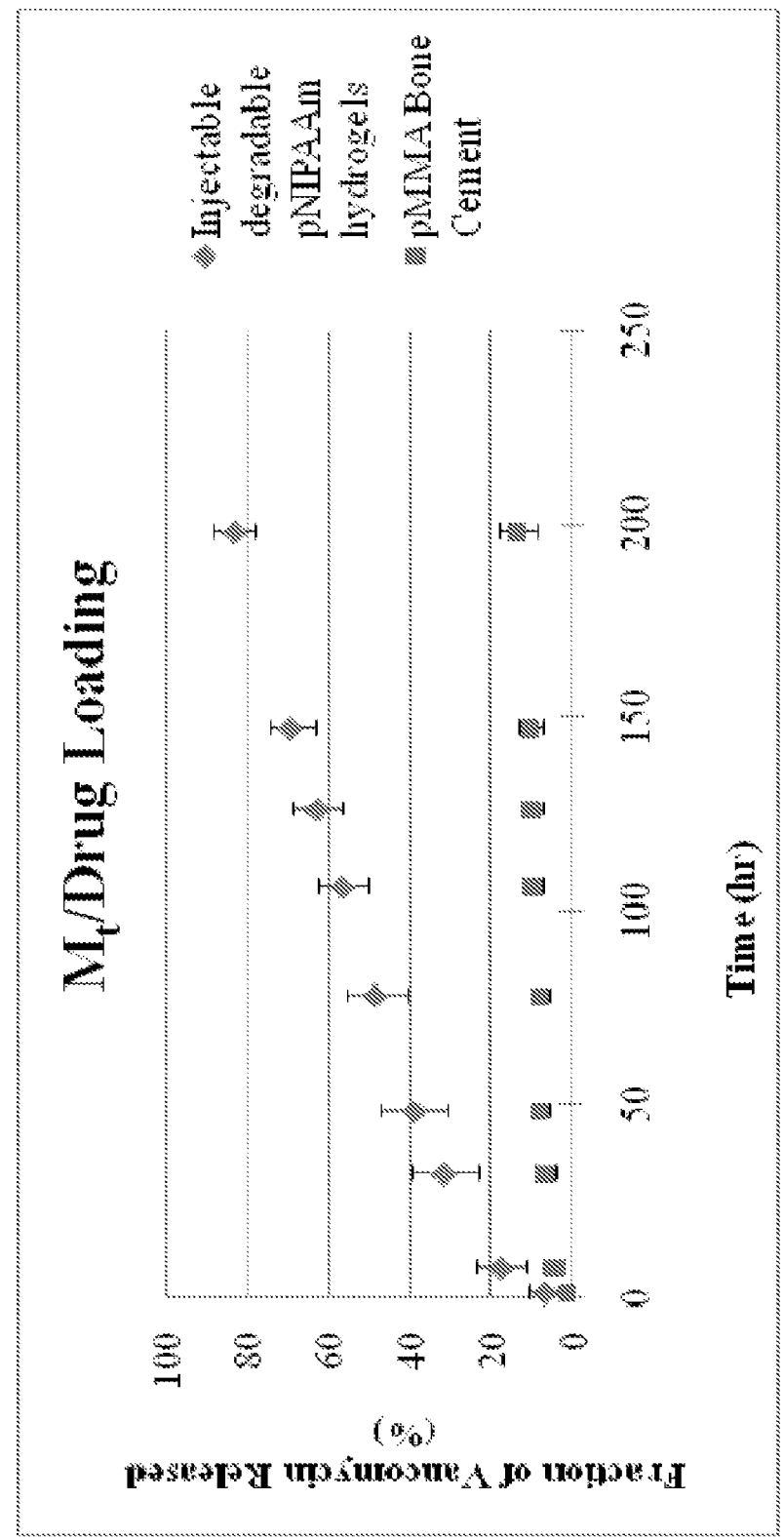
FIG. 6 graphically illustrates an amount of vancomycin released as a fraction of the drug loaded.

FIG. 6 graphically illustrates an amount of vancomycin released as a fraction of the drug loaded. Most of the drug that is loaded into bone cement is not released whereas Applicants' injectable and degradable terpolymer I based gels comprising poly(NIPAAm-co-DBLA-co-JAAm) release nearly all of the drug loaded into them within 8 days.

Figure 7:
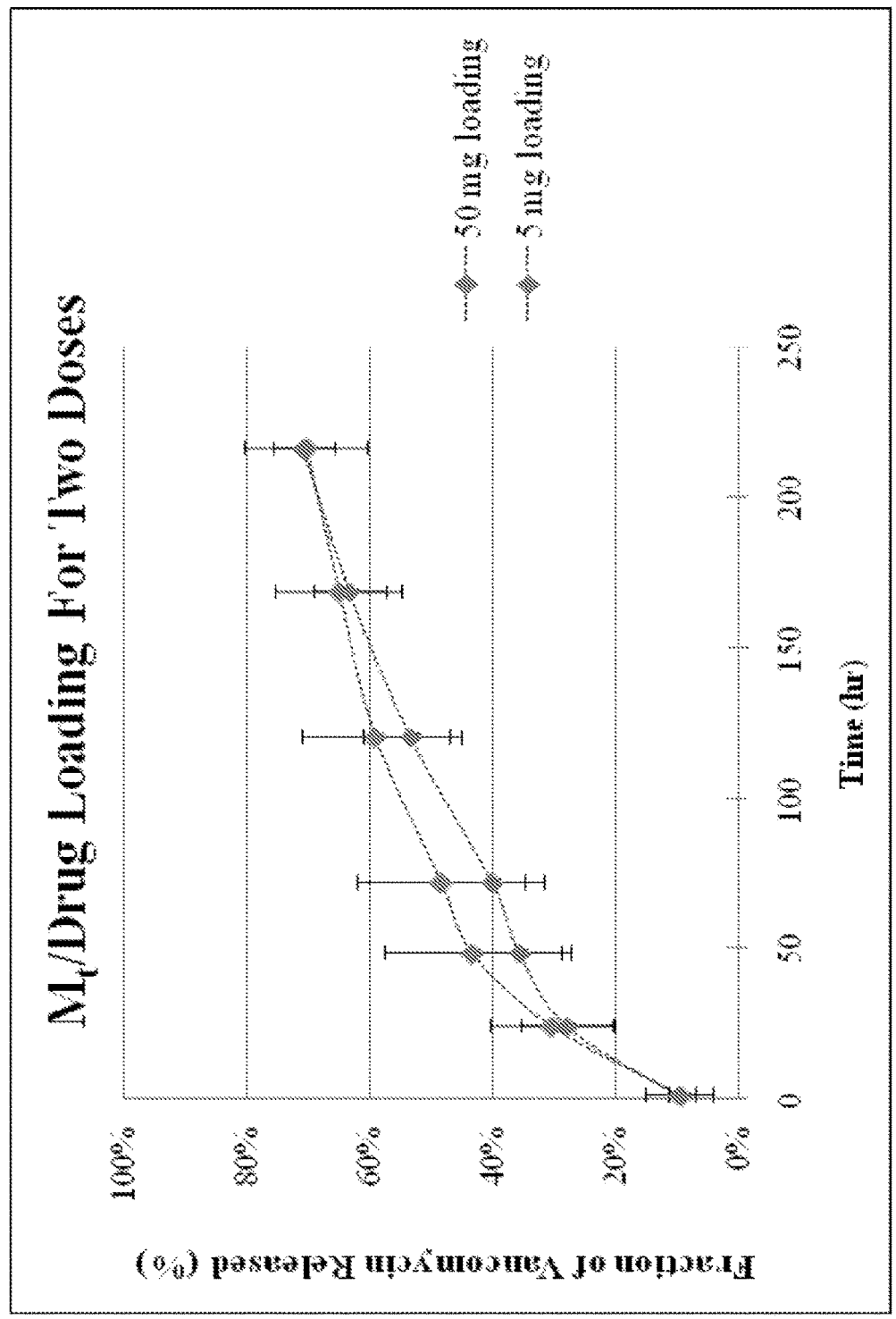
FIG. 7 graphically illustrates a fraction of loaded vancomycin released from Applicants' injectable and degradable terpolymer I based gels comprising poly(NIPAAm-co-DBLA-co-JAAm) gels loaded with either 50 mg or 5 mg per gel.

FIG. 7 graphically illustrates a fraction of loaded vancomycin released from Applicants' injectable and degradable terpolymer I based gels comprising poly(NIPAAm-co-DBLA-co-JAAm) gels loaded with either 50 mg or 5 mg per gel. Some vancomycin is insoluble when loaded into the polymer solution at 50 mg/mL. The similarity between these curves indicates that the polymer, as opposed to the drug solubility, is primarily responsible for controlling the rate of drug release.

Figure 8:
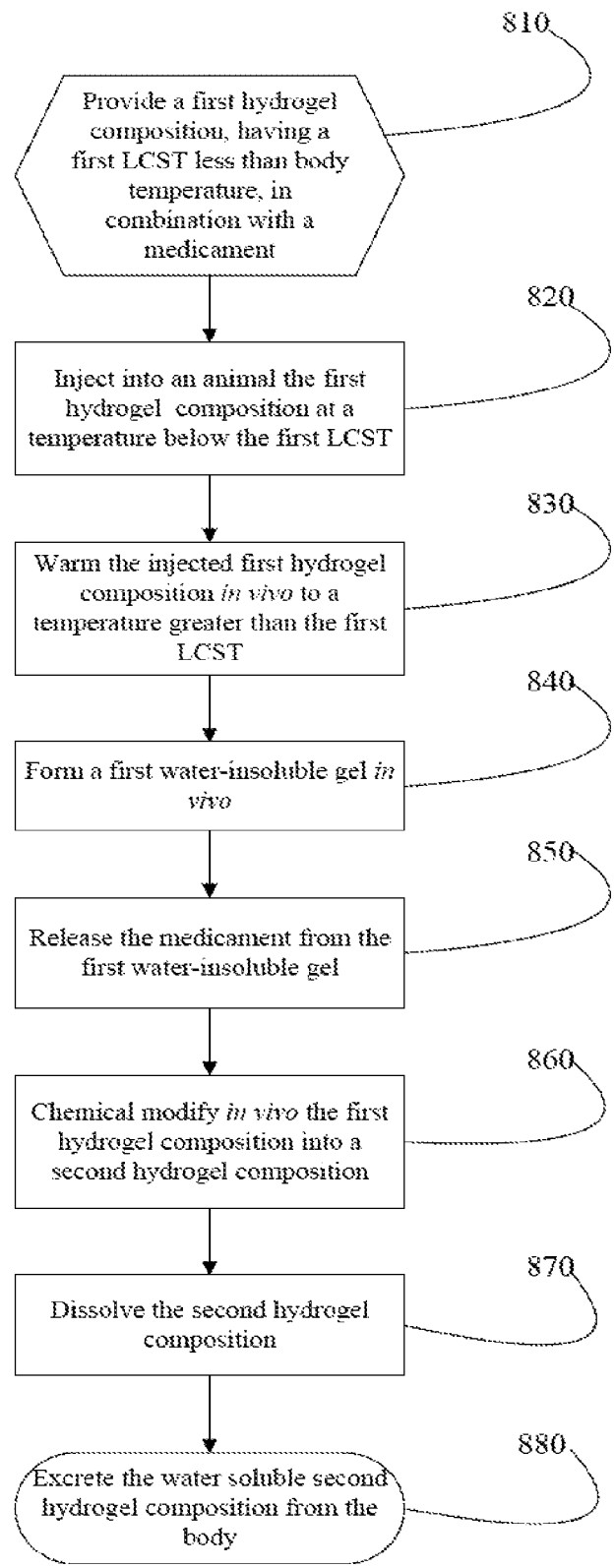
FIG. 8 summarizes Applicants' method to deliver a medicament to an injection site within the body of an animal, including a human.

FIG. 8 summarizes Applicants' method to deliver a medicament to an injection site within the body of an animal, including a human. In certain embodiments, the injection site comprises the surface of an bone implant. Referring now to FIG. 8, in step 810 the method provides a medicament and a first hydrogel comprising a first LCST less than the body temperature of the subject animal. Those skilled in the art will appreciate, that body temperature for a human is about 37° C. In these human injection embodiments, the first hydrogel of step 810 comprises a LCST less than about 37° C.

By medicament, Applicants mean a material selected from the group consisting of a Nucleic acid, a Protein (including growth factors, bone morphogenetic proteins), a Polypeptide, a Contrast agent for imaging, an Anesthetic, an Antineoplastic agent, an Antifungal, an Anti-inflammatory drug (steroids, non-steroidal anti-inflammatory drugs (NSAIDs), and an Antibiotic. In certain embodiments, the Antibiotic comprises one or more of Aminoglycosides, including gentamicin, amikacin, and tobramycin, Cephalosporins including cefazolin, Vancomycin, and Rifampin In certain embodiments, the first hydrogel of step 810 comprises a polymeric material comprising a backbone formed from polymerization of one or more substituted acrylamides, one or more monomers containing one or more hydrolyzable linkages, and a monomer comprising a water soluble polymer moiety attached thereto.

In certain embodiments, the first hydrogel of block 810 comprises Applicants' hydrogel I. In certain embodiments, the first hydrogel of block 810 comprises Applicant's hydrogel formed from N-isopropylacrylamide, JEFFAMINE M-1000 acrylamide (JAAm), and acryloyloxy-β,β-dimethyl-γ-butyrolactone. In certain embodiments, the first hydrogel of step 810 comprises Applicant's hydrogel comprising poly(NIPAAm-co-DBLA-co-JAAm) with 5.9 mol % DBLA and 2.3 mol % JAAm.

In block 820, an aqueous solution of the medicament and the first hydrogel of block 810 is injected into a selected animal at a temperature less than the first LCST. In certain embodiments, the injection site comprises a tissue space wherein a subsequently formed gel will substantially completely fill that tissue space. In certain embodiments, the first hydrogel of block 810 is utilized in conjunction with implantation of an artificial joint. In certain of these embodiments, the injection of block 820 is performed after implantation such that the injected hydrogel is disposed adjacent a surface of the implanted artificial joint.

In certain embodiments, the hydrogel of block 810 is coated onto a surface of an artificial joint prior to implantation. In these embodiments, the "injection" of block 820 comprises implantation of the artificial joint comprising a surface coated with the first hydrogel of block 810.

In block 830, the first hydrogel of block 810 injected into the body of an animal in block 820 is warmed in vivo to a temperature greater than the first LCST. In certain embodiments, the warming of block 830 is performed by the body heat of the animal. In certain embodiments, the warming of block 830 is performed by disposing a heating object, such as for example and without limitation, a heat lamp, a heating pad, hot compress, and the like, directed in near proximity to the injection site.

In block 840, the first hydrogel of block 810 injected into the body of an animal in block 820 and warmed in vivo to a temperature greater than the first LCST in block 830, forms in vivo a water-insoluble gel. In certain embodiments, the water-insoluble gel of block 840 is formed in, and substantially fills, a tissue space. In certain embodiments, the water-insoluble gel of block 840 is disposed on, and in near vicinity to, a surface of a joint implant.

In block 850, the water-insoluble gel of block 840 releases the medicament of block 810 into tissues adjacent the injection site of block 820. In certain embodiments, the release of medicament is sustained over time. In certain embodiments, the aggregate amount of medicament released from the water-insoluble gel of block 840 into the injection site of block 820 plotted on a Y axis of a graph against time plotted on an X axis of the graph over time can be approximately modeled by a linear equation of the type y=mx+b, wherein m is slope of the straight line and b is the intercept of the straight line with the Y axis. As a general matter, the intercept is 0.

In other embodiments, the release is approximately proportional to the square root of time over the first 60% of release, with a slower rate of release thereafter.

In block 860, the first hydrogel of block 810 which was injected in block 820 is chemically modified to form a second hydrogel having a second LCST, wherein the second LCST is greater than body temperature. For example, in certain embodiments, the pendent ester moieties of the plurality of repeat units IV are hydrolyzed in vivo to convert first terpolymer I injected in block 820 and gelled in block 840 to a second terpolymer XXII, wherein R9 comprises a pendent hydroxyl group or a pendent carboxylic acid group resulting from a hydrolysis of an acid moiety or an anhydride moiety, respectively, in pendent group R8.

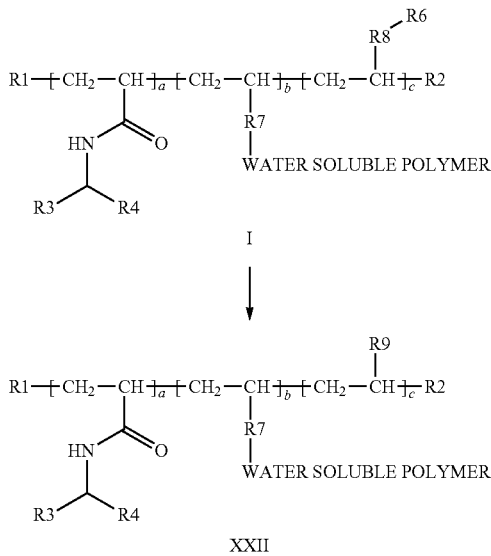

I

XXII

In certain embodiments wherein R6 comprises a substituted butyrolactone moiety and R8 is an ester linkage, the pendent substituted butyrolactone moieties of the plurality of repeat units IV are hydrolyzed in vivo to convert first terpolymer I injected in block 820 and gelled in block 840 to a second terpolymer XXIII, wherein R9 comprises a carboxylic acid moiety.

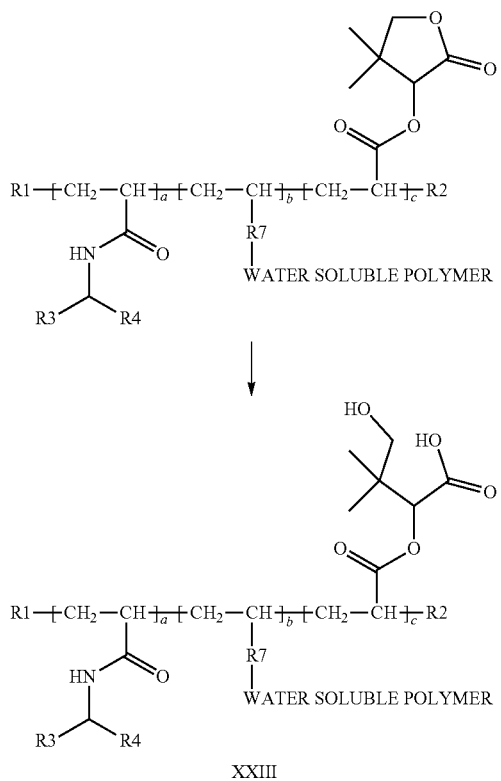

XXIII

In certain embodiments, in block 860 the first hydrogel of block 810 is converted into a second hydrogel XXII/XXIII that is water soluble at body temperature.

In block 870, the water soluble second hydrogel dissolves in body fluids.

In block 880, the second hydrogel of step 870 is excreted from the body.

Using the method of FIG. 8, a first hydrogel having a LCST less than body temperature and a medicament, in aqueous solution, are injected into the body of an animal. The first hydrogel is warmed to a temperature greater than its LCST, and a water-insoluble gel is formed. The medicament is released over time from the water-insoluble gel. Thereafter, the first hydrogel is converted in vivo into a second hydrogel having a LCST greater than body temperature. This second hydrogel is water soluble, and is carried by the animal's circulatory system to its kidneys. The second hydrogel is then excreted from the body.

While the preferred embodiments of the present invention have been illustrated in detail, it should be apparent that modifications and adaptations to those embodiments may occur to one skilled in the art without departing from the scope of the present invention as set forth in the following claims.

We claim:

1. A polymer for preparing a hydrogel, wherein the polymer is poly(NIPAAm-co-DBLA-co-JAAm) having a structure of:

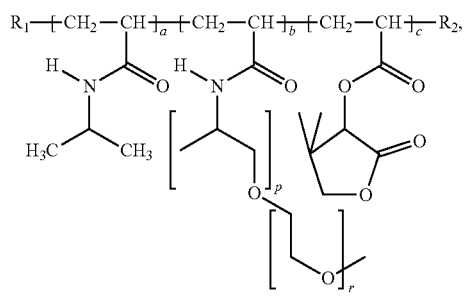

wherein:
R1 and R2 are independently selected from the group consisting of H, alkyl, phenyl, benzyl, 2-cyanoprop-2-yl, 4-cyanopentanoic acid-4-ylethyl-2-propionate, sulfate, 2-[2-methoxypropan-2-yl)oxy]propan-2-yl, and 4-cyano-4-(ethylsulfanylthiocarbonyl)sulfanylpentanoic acid;
a is about 10 to about 1,000, b is about 1 to about 250, and c is about 1 to about 500, and units of a, units of b, and units of c are arranged randomly and/or in blocks;
a ratio of r:p is 19:3; and
r is about 5 to about 2,500 and p is about 1 to about 1,000, and units of r and units of p are arranged randomly.

2. The polymer of claim 1, wherein the units of r and the units of p are a random copolymer with a weight of about 1,000 Da.

3. The polymer of claim 1, comprising the DBLA at about 4.7 mol % and JAAm at about 2.9 mol %.

4. The polymer of claim 1, the polymer having a number average molecular weight Mn of about 13,100 g/mol.

5. The polymer of claim 1, the polymer having a weight average molecular weight Mw of about 28,200 g/mol.

6. A hydrogel comprising:
the polymer of claim 1; and
water.

7. The hydrogel of claim 6, wherein the units of r and the units of p are a random copolymer with a weight of 1,000 Da.

8. The hydrogel of claim 6, comprising the DBLA at about 4.7 mol % and JAAm at about 2.9 mol %.

9. The hydrogel of claim 6, the polymer having a number average molecular weight Mn of about 13,100 g/mol.

10. The hydrogel of claim 6, the polymer having a weight average molecular weight Mw of about 28,200 g/mol.

* * * * *